(12) United States Patent
Meot (10) Patent No.: US 7,109,502 B1
(45) Date of Patent: Sep. 19, 2006

(54) DEVICE FOR IRRADIATING A TARGET WITH A HADRON-CHARGED BEAM, USE IN HADRONTHERAPY

(75) Inventor: Francois Meot, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 95 days.

(21) Appl. No.: 10/517,773

(22) PCT Filed: Jun. 30, 2003

(86) PCT No.: PCT/FR03/02026

§ 371 (c)(1),
(2), (4) Date: Dec. 27, 2004

(87) PCT Pub. No.: WO2004/004832

PCT Pub. Date: Jan. 15, 2004

(30) Foreign Application Priority Data

Jul. 2, 2002 (FR) .................................. 02 08240
Jul. 23, 2002 (FR) .................................. 02 09330

(51) Int. Cl.
*H01J 37/141* (2006.01)

(52) U.S. Cl. ............. 250/492.3; 250/398; 250/396 ML (58) Field of Classification Search ............. 250/492.3, 250/398, 396 ML, 396 R
See application file for complete search history.

(56) References Cited

U.S. PATENT DOCUMENTS

| | | | |
|---|---|---|---|
| 4,962,317 A | 10/1990 | Jason et al. | |
| 5,039,867 A | 8/1991 | Nishihara et al. | |
| 6,693,283 B1 * | 2/2004 | Eickhoff et al. | 250/396 ML |
| 6,717,162 B1 * | 4/2004 | Jongen | 250/505.1 |

FOREIGN PATENT DOCUMENTS

| | | |
|---|---|---|
| WO | 00/40064 | 7/2000 |
| WO | 02/41948 | 5/2002 |

OTHER PUBLICATIONS

Futami, Yasuyuki et al. "Broad-beam three-dimensional irradiation system for heavy-ion radiotherapy at HIMAC", Nuclear Instruments and Methods in Physics Research A, vol. 430, No. 1, pp. 143-153.
Jones, W.P. et al. "Design of a Beam Transport System for a Proton Radiation Therapy Facility". Proceedings of the 1999 Particle Accelerator Conference, pp. 2519-2521 1999.
Meot, F. et al. "Principles of the non-linear tuning of beam expanders", Nuclear Instruments and Methods in Physics Research A, vol. 379, No. 2, pp. 196-205, XP002235833 1996.
Kitagawa, A. et al. "The Medical Accelerator HIMAC and the Charged Particle Therapy in Japan", Proc. PAC Conf. 2001.
Gross, K.D. et al. "Proposal for a dedicated ion beam facility for cancer therapy", GSI 1998.

(Continued)

*Primary Examiner*—Kiet T. Nguyen
(74) *Attorney, Agent, or Firm*—Oblon, Spivak, McClelland, Maier & Neustadt, P.C.

(57) ABSTRACT

A device for irradiating a target by a charged hadron beam, which may find application in hadron therapy. The device includes corpuscular optics designed to make the density of the beam uniform, along at least one direction perpendicular to the trajectory of the beam, and a three-dimensional control for the irradiation.

11 Claims, 3 Drawing Sheets

OTHER PUBLICATIONS

Blind, Barbara. "Generation of a Rectangular Beam Distribution for Irradiation of the Accelerator Production of Tritium Target", Report MS H811, pp. 453-455.

Meot, F. et al. "On Beam Uniformization by Non-Linear Optics", Saturne National Laboratory Report, pp. 1-20 1995.

Urakabe, Eriko. "Spot Scanning Irradiation with 11C Beams at HIMAC", FFAG-02 Workshop 2002.

Molodojentsev, Alexandre et al. "Flexible Computational Model of Pencil Beam Dose Distribution for Spot-Scanning". FFAG-02 Workshop 2002.

Itano, Akifumi., Accelerator Facility PATRO for Hadrontherapy at Hyogo Ion Beam Medical Center.

* cited by examiner

FIG. 6

DEVICE FOR IRRADIATING A TARGET WITH A HADRON-CHARGED BEAM, USE IN HADRONTHERAPY

TECHNICAL DOMAIN

This invention relates to a device for irradiation of a target by a charged hadron beam, more simply referred to as "hadrons" in the following.

In particular, it relates to a device for irradiation of a part of the human body during a hadrontherapy session, this area being occupied by a tumour.

The invention is used for applications in all fields that require irradiation of a target that is inaccessible or difficult to access.

For example, it is applicable to irradiation of radioactive waste placed in a hermetically sealed container in order to transmute this waste.

The invention is more particularly applicable to hadrontherapy.

It could be installed in all hadrontherapy centres and it could replace techniques used at the moment to irradiate tumours by hadron beams.

STATE OF PRIOR ART

Hadrontherapy is a therapeutic method based on the same principles as radiotherapy, except that it uses hadron beams while radiotherapy uses photons or electrons.

Light ions, for example such as $H^+$, $He^{2+}$ and $C^{4+}$ are usually used as the hadrons.

Beams of such ions are produced by an accelerator installation, usually a cyclotron for protons, or a synchrotron for heavier ions.

Hadrontherapy techniques are known from the following documents:

[1] "The medical accelerator HIMAC and the charged particle therapy in Japan", A. Kitagawa and F. Soga, Proc. PAC Conf. 2001, June 18–22 2001, Chicago, Ill., USA.

[2] "Proposal for a dedicated ion beam facility for cancer therapy", Eds. K. D. Gross, M. Pavlovic, GSI, Darmstadt, September 1998.

The advantage of hadrontherapy compared with radiotherapy is based on the existence of the physical phenomenon of "Bragg peak" according to which hadrons lose practically all their kinetic energy at a defined depth in the human body, thus causing a peak dose deposit at this location, called the "Bragg peak".

The depth of the Bragg peak depends on the kinetic energy of the incident beam and can therefore typically be adjusted to between one and several tens of centimeters, by accelerating hadrons to kinetic energies typically varying from 50 MeV/u to 450 MeV/u using a synchrotron, or by using a moment analysis system in the case of a proton beam accelerated with a cyclotron.

Concerning this Bragg peak phenomenon one will refer e.g. to document [2].

The advantage of light ions and particularly carbon ions compared with protons (H*) is based on their better biological efficiency that creates amplification of the Bragg peak.

The invention is useful for the two hadron beam production techniques using a synchrotron or cyclotron type accelerator. It could replace irradiation systems used in hadrontherapy centres, that are based on either of these two types of accelerators.

We will now reconsider known devices for irradiation of a tumour by a hadron beam.

The dimensions of a tumour can be as high as several centimeters. In existing installations, the tumour volume as a whole is irradiated in two different ways.

The first technique used was passive irradiation, that is still used at the present time since it has the advantage that it is well controlled and well known.

A second technique that is now under development is scanning by pixels or active scanning, that enables a three-dimensional irradiation conforming to contours of the tumour. This is why this technique is called the "3D conformational irradiation technique".

The passive irradiation technique is rather used with cyclotrons, that are fixed energy machines. Nevertheless, it is also used with synchrotrons (see document [1]).

In this second technique, the irradiation is spread in depth by spreading the Bragg peak, through the use of a scattering material that induces a large dispersion of the kinetic energy of the incident hadron beam. It was used following experimental works in order to make beams uniform by non-linear corpuscular optical means.

Further information about this subject is given in the following document:

[3] "Generation of rectangular beam distributions", B. Blind, Report MS H811, LANL, NM 87545.

The mathematical modelling of this technique was described by F. Méot and T. Aniel.

Further information on this subject is given in the following documents:

[4] "On beam uniformization by non-linear optics" F. Méot and T. Aniel, Saturne National Laboratory Report, Ref. CEA/DSM/GECA/GT/95-05, July 1995, pages 1 to 20.

[5] "Principles of the non-linear tuning of beam expanders", F. Méot and T. Aniel, Nuclear Instruments and Methods in Physics Research A379, 1996, pages 197 to 205.

In the case of passive irradiation, transverse irradiation of the tumour is obtained by transverse expansion of the beam, for example using a scanning system called a "wobulator" that extends the beam over the entire width of the tumour, by associating this scanning system with scattering materials, the purpose of which is to make the transverse density uniform, and with diaphragm systems, for example multi-slide collimators, the purpose of which is to define the contours of the area to be irradiated as well as possible.

The passive irradiation technique has at least three serious disadvantages.

Indeed it is based on the principle of degradation of the incident beam: starting from a high quality and practically single energy beam, a beam is formed with large dimensions and dispersed energy.

This technique also involves insertion of interception elements called "degrading materials", in the incident beam.

Furthermore, this technique has the major defect that it doest not enable precise 3D conformational irradiation: areas external to the tumour are inevitably irradiated.

The use of the active scanning technique is preferably envisaged in installations based on a synchrotron, which is a variable energy machine.

However, the obvious advantage of this technique means that it is now also developed near some cyclotron installations, which in the past were limited to passive irradiation, using a dispersion and moment analysis system which makes it possible to induce a wide energy range.

In this active scanning technique, a fine hadron beam is used with a diameter typically equal to a few millimeters and irradiation in depth is achieved by sections, by adjusting the energy of the hadron beam, which has the effect of determining the depth of the Bragg peak. Remember that the energy of hadrons corresponds to an irradiation depth of a few millimeters.

The transverse irradiation of a section of the tumour is achieved by scanning this section using the beam spot, in the same way as a television beam, at a speed of approximately 10 meters per second.

One preferred variant of this technique at the present time (see document [2]) consists of irradiating the section of the tumour pixel by pixel.

Given a depth and therefore a section, the spot is held on a pixel whose diameter is consequently the same as the diameter of the beam spot, until the required dose is obtained, and the spot is then quickly moved in translation to the next pixel, and so on.

Figure 1:
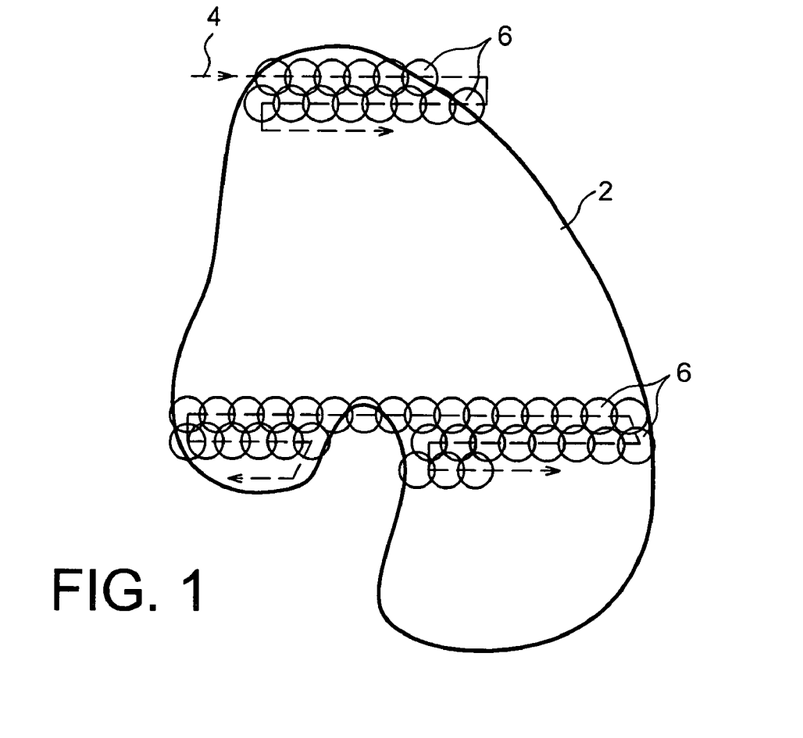
FIG. 1 diagrammatically illustrates irradiation of a tumour section by a known transverse pixel scanning technique, and has already been described.

This variant is diagrammatically illustrated in FIG. 1, that shows irradiation of a tumour section 2 by a hadron beam not shown, perpendicular to the plane of the figure. Transverse scanning of this section is represented by the dashed lines 4, and the pixels 6 are irradiated in sequence.

Compared with passive irradiation, active irradiation or active scanning has the important advantage that it enables 3D conformation and a more precise adjustment of the dose at any point in the volume to be irradiated, point that is also called the "volume pixel" or voxel.

Another transverse expansion and uniformisation technique in passive irradiation was recently proposed in the hadrontherapy field.

Refer to the following document for further information about this subject:

[6] "Design of a beam transport system for a proton radiation therapy facility", W. P. Jones and G. P. Berg, Proc. Particle Accelerator Conf., New-York, 1999, pages 2519–2521.

The advantage of this other technique is that it does not intercept the irradiation beam since it is based on a system composed solely of corpuscular optics devices: this system uses non-linear magnetic lenses, each lens being an octupole or a combination of an octupole and a dodecapole.

Note that this technique had been proposed in the past for the production of beams with a large (of the order of a square meter) and uniform transverse intensity distribution, for reprocessing of nuclear waste by irradiation.

Further information about this subject is given in document [3] mentioned above.

This avoided the use of scattering materials which have the disadvantage of tending to deteriorate the beam, since they generate lateral and distal scattering tails.

The current trend is to use the pixel scanning technique, since this is the only technique that enables three-dimensional conformational irradiation, also knowing that passive irradiation is still used mainly for historical reasons.

The pixel depth is then controlled via the energy of the incident beam, either by means of the accelerator for a synchrotron, or through degradation by means of interception materials.

Further information about this subject is given in the following documents:

[8] "Spot scanning irradiation with $^{11}$C beams at Himac", E. Urakabe, FFAG-02 Workshop, KEK, Tsukuba, February 13–15 2002.

[9] "Flexible computational model of pencil beam dose distribution for spot-scanning", A. Molodojentsev and T. Sakae, FFAG-02 Workshop, KEK, Tsukuba, February 13–15 2002.

In the case of active scanning, the current trend is limited to the improvement of the pixel scanning technique.

Another scanning technique comparable to that described in document [1], is described in the following document:

[10] "Accelerator facility PATRO for hadrontherapy at Hyogo Ion Beam Medical Center", A. Itano.

Presentation of the invention

The purpose of this invention is to irradiate the target in a better controlled manner than in prior art described above, by outputting ions within the exact volume of this target.

In particular, the purpose of the invention is to considerably improve the active scanning technique mentioned above.

Specifically, the purpose of this invention is a target irradiation device, particularly an area of the human body, by a charged hadron beam, this beam being produced by means of generating a charged hadron beam, this device being characterized by the fact that it comprises:

corpuscular optics means, designed to make the transverse density of the charged hadron beam uniform, along at least one direction perpendicular to the trajectory of this charged hadron beam, and means for the three-dimensional control of the irradiation of the target by this charged hadron beam.

According to one preferred embodiment of the device according to the invention, the corpuscular optics means comprise at least one non-linear corpuscular optics lens.

These corpuscular optics means may include two non-linear corpuscular optics lenses designed to make the transverse density of the charged hadron beam uniform, along two directions perpendicular to each other and to the trajectory of this charged hadron beam.

Preferably, each non-linear corpuscular optics lens is 2n-polar, where n is an integer equal to at least 4.

According to one preferred embodiment of the invention, the three dimensional control means include:

means of adjusting the energy of the generated charged hadrons and scanning means capable of displacing the charged hadron beam to make it scan the target along a narrow substantially rectangular band.

Preferably, the scanning means include a pair of magnetic dipoles.

According to a first particular embodiment of the device according to the invention, the charged hadron beam generation means comprise a synchrotron and the means used to adjust the energy of the generated charged hadrons are the means of adjusting the energy of the charged hadrons produced by this synchrotron.

According to a second particular embodiment of the device according to the invention, the means of generation of the charged hadron beam comprise a cyclotron and the means of adjusting the energy of the generated charged hadrons include moment analysis means.

Preferably, the scanning means are capable of causing the centre of the narrow band to follow a median line while lengthening or shortening this narrow band in order to follow the contours of the target.

In one particular embodiment of the invention, the corpuscular optics means are capable of varying the uniformisation of the transverse density of the charged hadron beam depending on the length and/or the width of the narrow band.

In one advantageous embodiment of the invention, the scanning means are capable of making the charged hadron beam scan the target at predetermined depths of this target, and a plurality of times for each of these depths, the dose delivered to the target each time being equal to the total dose required for this depth, divided by the number of times.

The charged hadrons used in this invention are preferably light ions or more specifically light nuclei, in other words nuclei with an atomic number of typically less than 20.

For example, these nuclei are chosen among H+, He++, and C4+.

BRIEF DESCRIPTION OF THE DRAWINGS

This invention will be better understood after reading the description of example embodiments, given below for information only and in no way limitative, with reference to the appended drawings wherein.

DETAILED PRESENTATION OF PARTICULAR EMBODIMENTS

Figure 2:
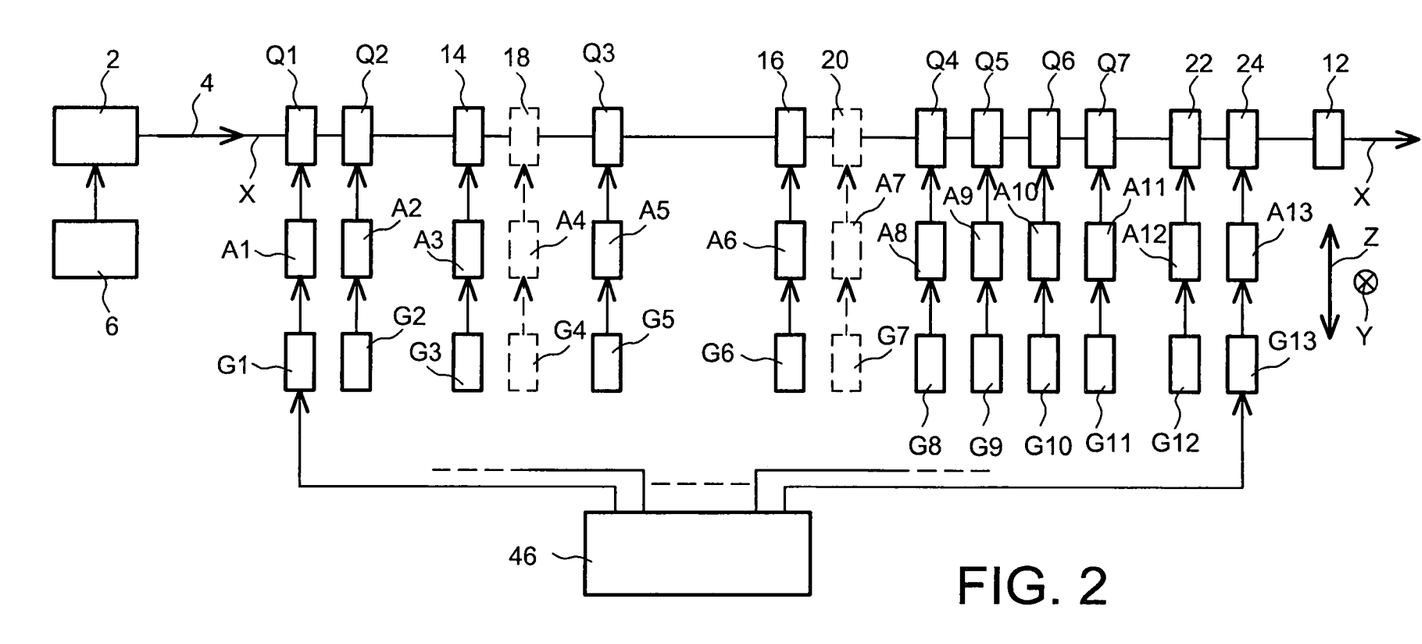
FIG. 2 is a diagrammatic view of a particular embodiment of the device according to the invention.

One particular embodiment of the device according to the invention is shown diagrammatically in FIG. 2.

This device is designed to act on a charged hadron beam, the trajectory of which extends along an X-axis.

Two directions Y and Z are also defined perpendicular to each other and to the X-axis. For example, the X-axis is horizontal, the Y-direction is also horizontal and the Z direction is vertical.

In the example shown in FIG. 2, the means of generating the hadrons beam 4 are composed of a synchrotron provided with means 6 of adjusting the energy of the hadrons. For example, these hadrons may be He$^{2+}$ or C$^{4+}$ nuclei.

Figure 3:
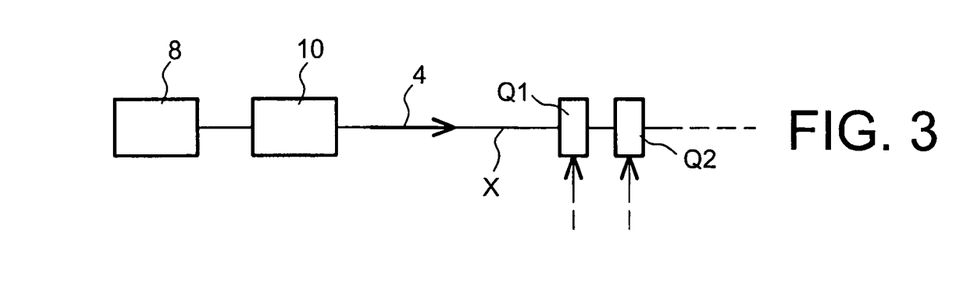
FIG. 3 is a diagrammatic and partial view of a variant of the device in FIG. 2.

In one variant that is diagrammatically and partially illustrated in FIG. 3, the hadrons are protons (H$^+$) and the protons beam generation means 4 are composed of a cyclotron 8.

This cyclotron is followed by moment analysis means 10 that adjust the energy of protons.

The target 12, for example a tumour, that is to be irradiated by the hadrons beam 4, can also be seen.

The device according to the invention shown in FIG. 2 is installed between the synchrotron 2 and the target 12 (and between the moment analysis means 10 and this target in the case of FIG. 3).

Along the X-axis, this device includes at least one non-linear uniformisation lens, at least one magnetic scanning dipole and a set of focussing lenses.

In the example, each non-linear uniformisation lens is an octupolar lens and two of them are used, references 14 and 16.

The octupolar lens 14 (respectively 16) is designed to make the transverse density of the hadrons beam 4 uniform along the horizontal Y direction (respectively the vertical direction Z).

A dodecapolar lens 18 can be added to the octupolar lens 14, and a dodecapolar lens 20 can be added to the octupolar lens 16.

In the example, two magnetic dipoles or magnetic dipolar magnets are used, marked with references 22 and 24.

They are preferably placed less than 10 m from the target 12.

The magnetic dipole 22 is designed to make the hadrons beam 4 scan the target 12 along the Y horizontal direction, and the magnetic dipole 24 is designed to make the hadrons beam 4 scan the target 12 along the vertical direction Z.

In the example, the focusing lenses are quadrupolar lenses numbered Q1 to Q7 respectively.

In this example we have: lens Q1 (divergent), lens Q2 (convergent), lens 14, lens 18 if provided, lens Q3 (divergent), lens 16, lens 20 if provided, lens Q4 (convergent), lens Q5 (divergent), lens Q6 (convergent), lens Q7 (divergent), dipole 22 and dipole 24, all in this sequence.

The device in FIG. 2 is classified in the category of active irradiation devices. Therefore, it has the important advantage of precise 3D conformation, while providing major improvements. The same is true for the variant in FIG. 3.

This device belongs to active scanning devices like those described above, in that irradiation by the beam 4 is actually controlled in three dimensions in space by means of scanning dipoles 22 and 24 that are placed a few meters on the upstream side of the tumour, and means of adjusting the energy of the incident beam 4.

Concerning the transverse distribution of the beam, let us add that the irradiated transverse area is extended into a narrow band with uniform density in one of the two directions Y and Z or in both directions, and in principle with a length equal to the local width of the section of the tumour being irradiated.

In the invention, a corpuscular optics device is used that therefore does not intercept the hadrons beam. It comprises one or two non-linear lenses.

In the example in FIG. 2, the two non-linear lenses 14 and 16 called uniformisation lens are used, integrated into the optical line that transports the hadrons beam to a patient whose tumour is to be irradiated.

A beam scanning device is also used that in the example comprises the two magnetic dipoles 22 and 24. These dipoles are of the type used for active scanning.

Admittedly, the transverse uniformisation technique making use of one or two non-linear lenses (see documents [3] and [6] mentioned above), and the beam scanning technique using a pair of magnetic dipoles, are already known.

However, this invention combines these two techniques in quite an innovative and advantageous manner.

We will now reconsider the transverse uniformisation used in the invention by means of a non-linear corpuscular optics device.

In its natural form (at the output from the synchrotron 2 or from moment analysis means 10), the beam 4 has a transverse density in the form of a bell (like a gaussian curve) in each of the two directions Y and Z, that are orthogonal to its propagation direction X.

But in the invention, it is essential that this density should be uniform, at least in one of the two directions Y and Z, or possibly in both.

This uniformisation is achieved by means of non-linear lenses, using one lens per direction.

2n-polar lenses are used, in which the order 2n is a sufficiently high even integer to obtain the required uniformisation, where 2n is preferably equal to 8 (octupolar lenses) or is more than 8 if necessary.

As we have already seen, complex non-linear lenses can even be used each formed by a pair of non-linear lenses, namely a 2n-polar lens and a 2m-polar lens, where m>n≧4, for example choosing n=4 and m=6.

FIG. 2 shows an optical line that achieves such uniformisation in the XY plane and in the XZ plane, as an example.

Figure 4:
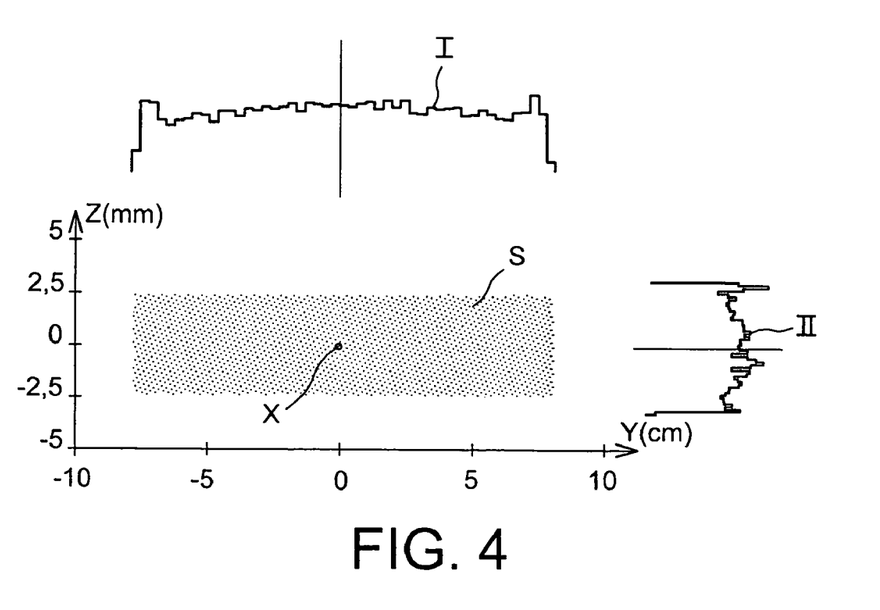
FIG. 4 is a cross sectional view of an irradiation beam that can be used in the invention, FIG. 5 diagrammatically illustrates irradiation of a tumour section by uniform, slow and two-dimensional scanning of this section, according to the invention, and FIG. 6 diagrammatically illustrates a juxtaposition of pixels to make a dose deposit uniform, in accordance with a known irradiation technique.

The cross section S of the beam 4 that is perpendicular to the X axis and forms a substantially rectangular band (the length of which being parallel to the Y direction and the width being parallel to the Z direction) together with the resulting profiles of the beam along Y (curve I) and along Z (curve II) are shown diagrammatically in FIG. 4 (given purely for guidance purposes and in no way limitatively, particularly concerning the indicated dimensions).

In the case of an optical line designed to implement uniformisation according to the invention, the corpuscular optics means of this line are provided as a function of the use of the non-linear lenses.

If a device conforming with the invention is installed on an existing optical line, it may be sufficient to adapt optical focusing adjustments to take account of constraints related to the positioning of non-linear lenses; it may be necessary to displace focusing quadrupoles included in the optical line.

We will now reconsider two-dimensional scanning.

Figure 5:
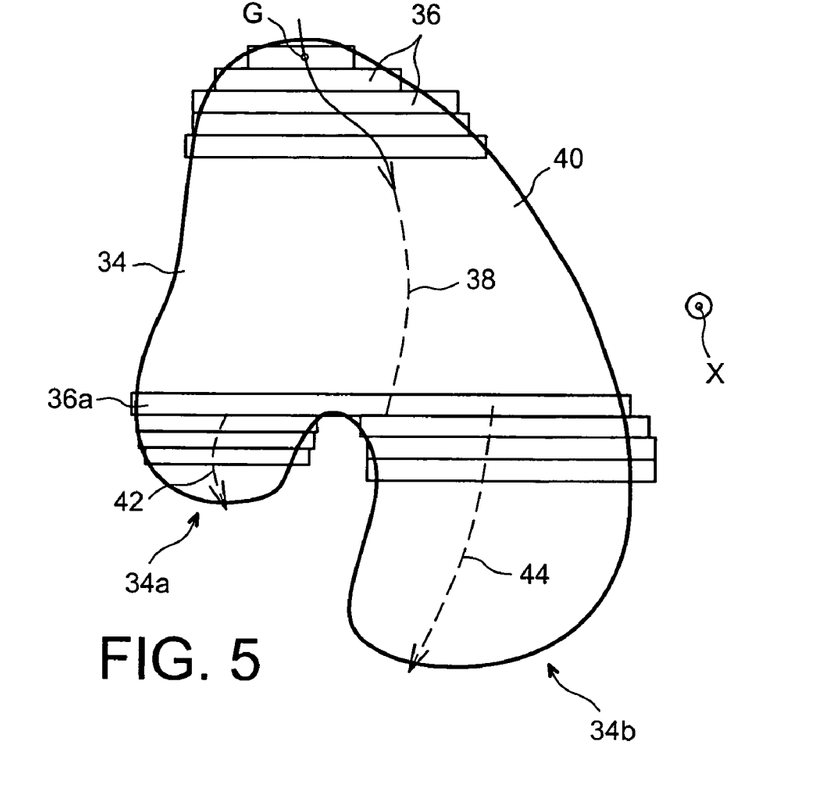

The device in FIG. 2 uses a slow guidance system for the beam 4 (in the sense that it is slower than in the case of active scanning), using the two dipole magnets 22 and 24, for example arranged just on the downstream side of the last quadrupole Q7 of the optical line in FIG. 2, such that the impression of the rectangular beam as shown diagrammatically in FIG. 4, slowly scans the tumour section considered, as shown diagrammatically in FIG. 5.

In this figure, the tumour section is marked with reference 34. A uniform, slow and two-dimensional scanning is carried out on it, by the hadrons beam, for which the section perpendicular to the X-axis is substantially in the shape of a rectangle 36: the centre of gravity G of this rectangle follows a median line 38 at the same time as the rectangle becomes longer or shorter to follow the contours 40 of the tumour.

Note that the rectangle slides and the contours of the area thus scanned are smooth, unlike what is shown in FIG. 5.

Furthermore, in the example in this FIG. 5, the bottom of the tumour is divided into two parts 34a and 34b.

In this case, starting from a scanning rectangle 36a, the scanning line 38 is firstly prolonged by a scanning line 42 to scan one 34a of these two parts by adapted scanning rectangles, and rectangle 36a is then used again to prolong the scanning line 38 by another scanning line 44 in order to scan the other part 34b by adapted scanning rectangles.

The length of the rectangle at the current point is adjusted in a very conventional manner using quadrupolar focussing lenses (for example quadrupoles Q4 to Q7). Its width is also adjustable at will, using the same quadrupoles. These are simple formations of images on the image plane of the optical line, which is the plane of the irradiated tumour section.

This requires simultaneous adjustment of the non-linear lens or both lenses, since uniformisation also depends on the adjustment of the quadrupoles (see document [4]).

All of this can be made conventionally using function generators that control power supplies for these various lenses and are themselves controlled by a software.

In FIG. 2, references A1 to A13 denote power supplies associated with components Q1, Q2, 14, 18, Q3, 16, 20, Q4, Q5, Q6, Q7, 22 and 24 respectively.

References G1 to G13 denote function generators that control these power supplies A1 to A13 respectively and reference 46 denotes electronic processing means containing the software and designed to control these function generators.

The data for this software are determined from the planning for the patient's treatment, produced by doctors in advance, after seeing images obtained by one or several imagery techniques known to those skilled in the art.

The following describes various advantages and the innovative nature of the invention.

Scanning by uniformised rectangle as described encompasses pixel scanning since a pixel can be considered as a small rectangle.

Furthermore, pixel scanning is now the preferred technique since it enables so-called "3D conformational", irradiation: the position and energy of the particle beam can be adjusted so as to reach a pixel with an arbitrary position in the volume of the tumour.

Furthermore, scanning by pixel, stopping on each pixel, is preferred instead of continuous television type scanning.

Therefore, in order to demonstrate the advantages of the invention compared with all known techniques, it is sufficient to compare the performances of the invention with the performances of active pixel scanning only, which is the prior art closest to the invention.

1/Firstly Consider the Question of Overintensities

Under some accident conditions, the hadrons beam may have an intensity time peak, which immediately stops irradiation by appropriate safety systems (not shown) known to those skilled in the art.

The result is more or less pronounced over-irradiation of the target area by the beam at this moment. This is a serious problem in hadrontherapy, and the optimum solution has not yet been found.

In the case of the device according to the invention, the irradiation rectangle usually has an area very much larger than the area of a pixel considered in the active scanning technique. This can easily be seen by comparing FIGS. 1 and 5, that show identical tumour sections.

Consequently, in the case of the invention as illustrated in FIG. 5, the accident peak causes a weaker surface over-irradiation than in prior art as illustrated in FIG. 1, the ratio of surface over-irradiations being proportional to the ratio of surface areas.

Therefore, the nuisance is lessened or even eliminated, knowing that irradiation involves non-linear effects with threshold phenomena such as the 2 Grays threshold (see document [1]).

2/Then Consider the Question of Dose Homogeneity

A)—The intensity of the beam extracted from the accelerator must be as constant as possible in time (for example expressing this intensity as a number of particles per second). In reality, this intensity is subject to fluctuations, within frequencies ranges that for example depend on accelerator extraction techniques.

The device according to the invention integrates these fluctuations, in other words smoothes them, better than is possible using the active scanning technique because scanning by rectangle is done at a lower speed: a rectangle equivalent to N pixels can be considered to remain stationary on a given area for N times longer than any of these N pixels.

B)—In pixel irradiation, the dose is made uniform between two adjacent pixels of the same line or between two pixels of successive lines, by an overlap of bell distributions that is considered to be appropriate.

Figure 6:
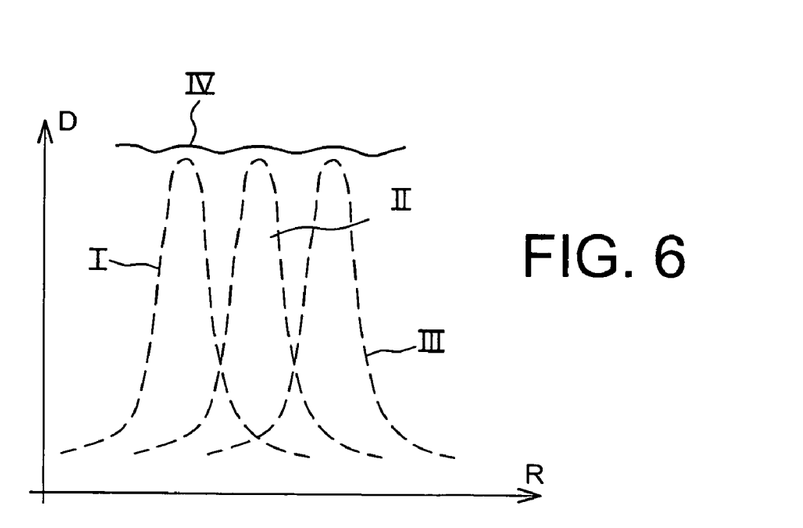

In this respect, consider FIG. 1 and FIG. 6 that diagrammatically illustrate how pixels are put adjacent to each other in order to make the dose deposit uniform.

Profiles I, II and III of three adjacent pixels are plotted in a coordinate system in which the position P is marked on the abscissa and the deposited dose D on the ordinate. The resulting profile has reference numeral IV.

The result is never guaranteed and also depends very closely on the transverse profile of the dose in each pixel, the distribution of which is not necessarily bell shaped or symmetrical.

The device according to the invention operates very differently. In the scanning direction, the dose deposit is made uniform by regulating the scanning speed by servo-control using measurement instruments not shown, identical to those used in the case of active scanning.

Further information about these instruments can be seen on documents [1, 2] mentioned above.

In the direction perpendicular to scanning, which is the direction of the length of the rectangle, uniformity is intrinsic. It is the result of uniformisation by the non-linear lenses.

3/In Addition Consider the Question of Moving Tumours

The fact that a tumour can move is one of the difficulties of hadrontherapy. Scanning by rectangle is also advantageous compared with pixel scanning in the case of an unexpected movement.

Indeed consider the worst case in which the movement of the tumour moves the current irradiation area away from the previously irradiated area. Then, for pixel scanning, a complete band is non-irradiated, while there is no lack of irradiation in the case of scanning by rectangle: the entire band was irradiated for the time interval preceding the movement, regardless of how short it is.

The following contains further details about the invention.

A bell-shaped profile in the scanning direction along Z can be left for an irradiation rectangle (see FIGS. 4 and 5). One of the two non-linear lenses is then inactive and uniformisation is only achieved in the other direction, namely the direction of the length of the rectangle.

A possible uniformisation in the direction of the width of the rectangle makes the distribution edges along this direction very abrupt (see histograms in FIG. 4) compared with a bell-shaped distribution.

This property can be used to obtain a better definition of the contours of the irradiated area.

Conversely, if these edges appear too abrupt, their slope can be modified in a controlled manner by acting on the appropriate non-linear lens.

This lens could also be switched on and off progressively at the ends of scanning to improve adaptation to the contours of the tumour.

In cyclotron installations, the conformational 3D irradiation technique is now being developed (for which synchrotrons are more suitable), using a moment analysis. Therefore, a device conforming to the invention can be used in such installations: all it is necessary is to put moment analysis means on the downstream side, as mentioned above.

Strictly speaking, the irradiation duration of a section is shorter with scanning by uniformised rectangle, than with pixel scanning:

1/Savings are Made in Displacement from One Pixel to the Next, and

2/Scanning by Rectangle is Continuous; it is Uninterrupted, Except Possibly at Some Changes in the Concaveness of the Tumour (as shown in FIG. 5).

Following the contours of a section to be irradiated is a difficult operation. Uniform scanning in rectangle provides a better adaptation: the length of the rectangle can be reduced and the scanning speed can be increased. On the contrary for pixel scanning, it is impossible to reduce the pixel diameter as much as we would like, otherwise uniformity between pixels can no longer be controlled.

With the invention, it is possible to do the scanning in several layers for a given depth (in other words in several passes), and possibly crosswise.

This can be done by dividing in the total dose necessary for this depth by the number of layers.

In this case, uniformisation of the dose is facilitated by carrying out steps, which enable adjustments, for example on the edges of the tumour. The advantages of scanning by rectangle already mentioned above are also slightly increased:

for overintensities, the intensity of an accident time peak will be further reduced, and the same is true for the resulting over-irradiation;

for dose homogeneity, the fluctuations of intensity with time related to slow extraction from a synchrotron, are even better smoothed;

for mobile tumours, if a tumour moves when a layer is being scanned, the existence of following or previous layers limits the lack of dose to a single layer.

The invention claimed is:

1. An irradiation device for a target, by a charged hadron beam, produced by means for generating a charged hadron beam, the device comprising:
    corpuscular optics means for making transverse density of the charged hadron beam uniform, along at least one direction perpendicular to a trajectory of the charged hadron beam; and
    means for three-dimensional control of irradiation of the target by the charged hadron beam,
    wherein the three dimensional control means includes:
        means for adjusting energy of generated charged hadrons, and
        scanning means for displacing the charged hadron beam to make it scan the target along a narrow substantially rectangular band, and for causing the center of the narrow band to follow a median line while lengthening or shortening the narrow band to follow contours of the target.

2. A device according to claim 1, wherein the corpuscular optics means comprises at least one non-linear corpuscular optics lens.

3. A device according to claim 2, wherein each non-linear corpuscular optics lens is 2n-polar, where 2n is an integer equal to at least 8.

4. A device according to claim 1, wherein the corpuscular optics means includes two non-linear corpuscular optics lenses configured to make the transverse density of the charged hadron beam uniform, along two directions perpendicular to each other and to the trajectory of the charged hadron beam.

5. A device according to claim 4, wherein each non-linear corpuscular optics lens is 2n-polar, where 2n is an integer equal to at least 8.

6. A device according to claim 1, wherein the scanning means includes a pair of magnetic dipoles.

7. A device according to claim 1, wherein the charged hadron beam generation means comprises a synchrotron and the means for adjusting the energy of the generated charged hadrons are means of adjusting the energy of the charged hadrons produced by the synchrotron.

8. A device according to claim 1, wherein the means for generation of the charged hadron beam comprises a cyclotron and the means for adjusting the energy of the generated charged hadrons includes moment analysis means.

9. A device according to claim 1, wherein the corpuscular optics means are capable of varying uniformization of transverse density of the charged hadron beam depending on a length and/or a width of the narrow band.

10. A device according to claim 1, wherein the scanning means is capable of making the charged hadron beam scan the target at predetermined depths of the target, a plurality of times for each of the depths, a dose delivered to the target each time being equal to a total dose required for the depth, divided by the number of times.

11. A device according to claim 1, wherein the charged hadrons are light nuclei.

* * * * *